US006521589B2

(12) United States Patent
Demeyere et al.

(10) Patent No.: US 6,521,589 B2
(45) Date of Patent: Feb. 18, 2003

(54) QUATERNARY FATTY ACID TRIETHANOLAMINE ESTER SALTS AND THEIR USE AS FABRIC SOFTENERS

(75) Inventors: Hugo Jean-Marie Demeyere, Merchtem (BE); Robert Otis Keys, Colombus, OH (US); Jans-Jürgen Köhle, Schlüchtern (DE); Johan De Poortere, Merelbeke (BE); Errol Hoffman Wahl, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/424,136

(22) PCT Filed: May 19, 1997

(86) PCT No.: PCT/US97/09130

§ 371 (c)(1),
(2), (4) Date: Dec. 22, 1999

(87) PCT Pub. No.: WO98/52907

PCT Pub. Date: Nov. 26, 1998

(65) Prior Publication Data

US 2002/0037825 A1 Mar. 28, 2002

(51) Int. Cl.[7] .................................................. C11D 1/62
(52) U.S. Cl. ..................................................... 510/527
(58) Field of Search ................................. 510/504, 519, 510/520, 522, 525, 527

(56) References Cited

U.S. PATENT DOCUMENTS

| | | | | | |
|---|---|---|---|---|---|
| 4,830,771 | A | * | 5/1989 | Ruback et al. | 252/8.8 |
| 5,437,801 | A | * | 8/1995 | Lueders et al. | 252/8.8 |
| 5,578,234 | A | * | 11/1996 | Corona, III et al. | 510/519 |
| 5,637,743 | A | * | 6/1997 | Contet et al. | 554/52 |
| 5,916,863 | A | * | 6/1999 | Iacobucci et al. | 510/329 |

FOREIGN PATENT DOCUMENTS

| | | |
|---|---|---|
| DE | 4101251 A1 | 7/1992 |
| DE | 4413431 A1 | 10/1995 |
| EP | 0 295 385 A1 | 12/1988 |
| EP | 0 550 361 A1 | 7/1993 |
| EP | 0 718 275 A1 | 10/1995 |
| WO | WO 91/01295 | 2/1991 |
| WO | WO 94/04643 | 3/1994 |
| WO | WO 94/20597 * | 9/1994 |

* cited by examiner

*Primary Examiner*—John Hardee
(74) *Attorney, Agent, or Firm*—Jason J. Camp; Kim William Zerby; Steven W. Miller

(57) ABSTRACT

The present invention relates to biodegradable softener compounds of the formula (1): $[(R)_{4-m}-N^{(+)}-[(CH_2)_n-Y-R^1]_m]X^{(-)}$ with an acid value of no more than 6.5. A process for making said compound is also provided. The softener can be incorporated into softener compositions to form solid and liquid compositions, including liquid dispersions and clear compositions.

15 Claims, No Drawings

QUATERNARY FATTY ACID TRIETHANOLAMINE ESTER SALTS AND THEIR USE AS FABRIC SOFTENERS

TECHNICAL FIELD OF THE INVENTION

The present invention relates to fabric softening compounds and composition thereof useful for softening fabrics. It especially relates to fabric softening compounds and/or compositions suitable for formulating textile softening compositions for use in the rinse cycle of a textile laundering operation to provide excellent fabric-softening/static-control benefits, the compositions being characterised by, e.g., reduced staining of fabric, excellent water dispersibility, rewettability, and/or storage and viscosity stability at subnormal temperatures, i.e., temperatures below normal room temperature, e.g., 25° C. The compositions of the invention are preferably liquid softening compositions, and more preferably, translucent or clear liquid softening compositions.

BACKGROUND OF THE INVENTION

Clear softening compositions are known in the art. For example, EP-A-0,404,471 discloses clear softening compositions with at least 20% by weight softener and at least 5% by weight of a short chain organic acid.

Formulating softening compositions which are clear is however not the only condition required of softening compositions. Indeed, such compositions are expected to provide an effective softening performance on the treated fabric. In this respect, EP-A-0,550,361 discloses softening compounds with specific molar ratios of fatty acid fraction to tertiary amine which provide effective softening performance without being detrimental to the fluidity and stability of composition containing said compound.

It is now an object to provide a softening compound which provides effective softening performance.

Still another object of the invention, is to provide a composition containing said compound which are clear but still not detrimental to the fluidity and stability of composition.

These objects have now surprisingly been met by producing the softening compound from the condensation of fatty acids with triethanolamine, wherein the condensation occurs for a period such that the condensation product has an acid value (AV) of less than 6.5, the condensation product subsequently being quaternized.

The AV of the compound is measured on the condensation product before the quaternisation step by the test method defined hereinafter.

For optimum softness benefit, it is preferred that the reactants are present in a molar ratio of fatty acid fraction to triethanolamine of from 1:1 to 2.5:1.

The finding that a lower acid value of the invention compound leads to higher softness performance when using the invention compound is very surprising and unexpected. Indeed, as known from GB 2,039,556, the addition of fatty acid provide an increase in the softness performance of the softening composition. The Applicant, in this respect, has found that the addition of fatty acid, instead of decreasing the acid value, increased the acid value. Accordingly, it was generally believed that the softness performance in relation to the acid value followed a curve showing a maximum at an AV above 10. To the contrary, it has been found that the softness performance followed a line whereby the higher the acid value, the less softening performance is obtained.

By effective softening performance, it is meant that the compound of the present invention provides better softening performance to fabrics compared to fabrics which have been treated with a similar compound but with an AV above 6.5. In a preferred embodiment, the compound of the invention provides better softness performance on treated fabrics therewith compared to compounds having the hereinbelow described molar ratios but not the specified AV.

SUMMARY OF THE INVENTION

The present invention relates to a biodegradable fabric softener compound comprising a quaternary ammonium salt, the quaternised ammonium salt being a quaternised product of condensation between:
a)-a fraction of saturated or unsaturated, linear or branched fatty acids, or of derivatives of said acids, said fatty acids or derivatives each possessing a hydrocarbon chain in which the number of atoms is between 5 and 21, and
b)-triethanolamine, characterised in that said condensation product has an acid value, measured by titration of the condensation product with a standard KOH solution against a phenolphtaleine indicator, of less than 6.5.

In a preferred embodiment of the invention, the fatty acid fraction and the triethanolamine are present in a molar ratio of from 1:1 to 2.5:1.

The present invention also relates to a process for making a softener compound, and in particular said compound.

Also provided herein is a softening composition containing said softening compound.

DETAILED DESCRIPTION OF THE INVENTION

I-Softener Compound

The essential component of the invention is a biodegradable fabric softener compound comprising a quaternary ammonium salt, the quaternised ammonium salt being a quaternised product of condensation between:
a)-a fraction of saturated or unsaturated, linear or branched fatty acids, or of derivatives of said acids, said fatty acids or derivatives each possessing a hydrocarbon chain in which the number of atoms is between 5 and 21, and
b)-triethanolamine,
characterised in that said condensation product has an acid value, measured by titration of the condensation product with a standard KOH solution against a phenolphtaleine indicator, of less than 6.5.

The acid value is preferably less than or equal to 5, more preferably less than 3. Indeed, the lower the AV, the better softeness softness performance is obtained.

The acid value is determined by titration of the condensation product with a standard KOH solution against a phenolphtaleine indicator according to ISO#53402. The AV is expressed as mg KOH/g.

For optimum softness benefit, it is preferred that the reactants are present in a molar ratio of fatty acid fraction to triethanolamine of from 1:1 to 2.5:1.

It has also been found that the optimum softness performance is also affected by the detergent carry-over laundry conditions, and more especially by the presence of the anionic surfactant in the solution in which the softening composition is used. Indeed, the presence of anionic surfactant that is usually carried over from the wash will interact with the softener compound, thereby reducing its performance. Thus, depending on usage conditions, the mole ratio of fatty acid/ triethanolamine can be critical. Accordingly, where no rinse occurs between the wash cycle and the rinse cycle containing the softening compound, a high amount of anionic surfactant will be carried over in the rinse cycle containing the softening compound. In this instance, it has been found that a fatty acid fraction/triethanolamine mole ratio of 1.4:1 to 1.8:1 is preferred. By high amount of anionic surfactant, it is meant that the presence of anionic in the rinse cycle at a level such that the molar ratio anionic surfactant/ cationic softener compound of the invention is at least 1/10.

Thus, according to another aspect of the invention, there is provided a method of treating fabrics which comprises the step of contacting the fabrics in an aqueous medium containing the softener compound of the invention or softening composition thereof wherein the fatty acid/triethanolamine mole ratio in the softener compound is from 1.4:1 to 1.8:1, preferably 1.5:1 and the aqueous medium comprises a molar ratio of anionic surfactant to said softener compound of the invention of at least 1:10.

Where, on the other hand, an intermediate rinse cycle occurs between the wash and the later rinse cycle, less anionic surfactant, i.e. less than 1:10 of a molar ratio anionic surfactant to cationic compound of the invention, will then be carried over. Accordingly, it has been found that a fatty acid/triethanolamine mole ratio of 1.8:1 to 2.2:1 is then preferred. Accordingly, in another aspect of the invention, there is provided a method of treating fabrics which comprises the step of contacting the fabrics in an aqueous medium containing the softener compound of the invention or softening composition thereof wherein the fatty acid/ triethanolamine mole ratio in the softener compound is from 1.8:1 to 2:1, preferably 2.0:1 and the aqueous medium comprises a molar ratio of anionic surfactant to said softener compound of the invention of less than 1:10.

Preferred compounds of the invention include compounds having the formula:

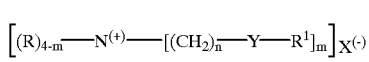

(1)

wherein each R substituent is hydrogen or a short chain $C_1$–$C_6$ alkyl or hydroxyalkyl group; preferably $C_1$–$C_3$ alkyl or hydroxyalkyl group, e.g., methyl (most preferred), ethyl, propyl, hydroxyethyl, and the like, benzyl, or mixtures thereof;

each m is in the range of 1 to 2.5;

each n is from 1 to 4; preferably 2;

each Y is —O—(O)C—, —(R)N—(O)C—, —C(O)—N(R)—, or —C(O)—O—; preferably —O—(O)C—; the sum of carbons in each $R^1$, plus one when Y is —O—(O)C— or —(R)N—(O)C— ("$YR^1$ sum"), is $C_6$–$C_{22}$, preferably $C_{12-22}$, more preferably $C_{14}$–$C_{20}$, (hereinafter, $R^1$ and $YR^1$ are used interchangeably to represent the hydrophobic chain, the $R^1$ chain lengths in general being even numbered for fatty alcohols and odd for fatty acids), but no more than one $R^1$, or $YR^1$, sum being less than 12 and then the other $R^1$, or $YR^1$, sum is at least 16, with each $R^1$ comprising a long chain $C_5$–$C_{21}$ (or $C_6$–$C_{22}$), branched alkyl or unsaturated alkyl, preferably $C_{10}$–$C_{20}$ (or $C_9$–$C_{19}$) branched alkyl or unsaturated alkyl, most preferably $C_{12}$–$C_{18}$ (or $C_{11}$–$C_{17}$) branched alkyl, or unsaturated alkyl, optionally substituted, For the unsaturated alkyl group, the Iodine Value of the parent fatty acid of this $R^1$ group is from 0 to 140, more preferably when used in clear softening composition the Iodine Value of the parent fatty acid of this $R^1$ group is from 50 to 130; whilst when used in dispersion the Iodine Value of the parent fatty acid of this $R^1$ group is preferably from 0 to 70 (As used herein, the "branched alkyl" groups include those that contain a substituent that is hydrophobic, even though they are attached to the main chain by bonds that are not carbon to carbon, e.g., by oxygen, as in the alkoxy substituents, and the Iodine Value of a "parent" fatty acid, or "corresponding" fatty acid, is used to define a level of unsaturation for an $R^1$ groups that is the same as the level of unsaturation that would be present in a fatty acid containing the same $R^1$ group. When an individual $R^1$ is both branched and unsaturated, it is treated as if it is branched.); and wherein the counterion, $X^-$, can be any softener-compatible anion; preferably, chloride, bromide, methylsulfate, ethylsulfate, sulfate, and/or nitrate, more preferably methylsulfate.

Also suitable as softener compounds according to the invention are those that are prepared as a single compound from blends of all the different branched and unsaturated fatty acids that are represented (total fatty acid blend), rather than from blends of mixtures of separate finished softener compound that are prepared from different portions of the total fatty acid blend.

It is preferred that at least a substantial percentage of the fatty acyl groups are unsaturated, e.g., from 25% to 70%, preferably from 50% to 65%. Polyunsaturated fatty acid groups can be used. The total level of active containing polyunsaturated fatty acyl groups (TPU) can be from 3% to 30%, preferably from 5% to 25%, more preferably from 10% to 18%. Both cis and trans isomers can be used, preferably with a cis/trans ratio of from 1:1 to 50:1, the minimum being 1:1, preferably at least 3:1, and more preferably from 4:1 to 20:1. (As used herein, the "percent of softener active" containing a given $R^1$ group is the same as the percentage of that same $R^1$ group is to the total $R^1$ groups used to form all of the softener actives.)

The mixed branched-chain and unsaturated materials are easier to formulate than conventional saturated branched chain fabric softener compounds. They can advantageously be used to form clear or translucent compositions.

II-Process for Making Said Compound

Another essential feature of the invention is a process for making a softener compound, in particular the softener compounds of the invention. This include the steps of:

a)-reacting the fatty acid fraction comprising fatty acids of formula $R^1COOH$ in which $R^1$ is a long chain $C_5$–$C_{21}$ branched alkyl or unsaturated alkyl, optionally substituted, with at least a triethanolamine, for a period such that the condensation product obtained compound has an acid value, measured by titration of the condensation product with a standard KOH solution against a phenolphtaleine indicator according to ISO#53402, of less than 6.5, and b)-reacting the condensation product thereby obtained with an alkylating agent, in the presence or absence of a solvent.

By fatty acid fraction, it is meant a mixture having fatty acids, fatty acid esters or mixtures therefore. This mixture can be either commercially available or provided by the reacting of a source of triglycerides. By reacting, it is meant the process of:

(a) hydrogenating a triglyceride product comprising a mixture of compounds of the formula (1)

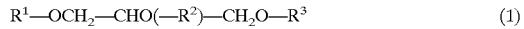

(1)

wherein $R^1$, $R^2$ and $R^3$ are acyl groups of which at least 1% contain 16 carbon atoms, and at least 70% contain 18 carbon atoms, provided that said acyl groups containing 18 carbon atoms include predominantly mono unsaturated acyl groups and minor amounts of saturated, diunsaturated and triunsaturated acyl groups, under hydrogenation conditions whereunder diunsaturated and triunsaturated acyl groups containing 18 carbon atoms are hydrogenated provided that formation of saturated acyl groups containing 18 carbon atoms is minimized;

(b) hydrolyzing the hydrogenated product of step (a) to form glycerine and a mixture of fatty acids based on said acyl groups.

The triglyceride source is preferably derived from vegetable oils and/or partially hydrogenated vegetable oils, such as, canola oil, safflower oil, peanut oil, sunflower oil, corn oil, soybean oil, tall oil, rice bran oil, etc and mixtures of these oils. One highly preferred triglyceride source which can be used herein is canola oil. Canola oil is a mixture of triglycerides having an appropriate chain length distribution and degree of unsaturation of the respective acyl groups. Canola oil is a particularly desirable starting product in accordance with the process of the present invention, for several reasons. In particular, its natural distribution of the chain lengths of the respective acyl groups has a notably high proportion of acyl groups containing 18 carbon atoms, thus avoiding the additional expense incurred when using other commercial sources of $C_{18}$ fatty acids as starting materials.

The triglyceride starting product can be hydrogenated, if desired, to convert diunsaturated and triunsaturated acyl groups, particularly those containing 18 carbon atoms, to their monounsaturated counterparts. It is normally desirable that hydrogenation of mono-unsaturated acyl groups is minimized and even completely avoided. Saturated acyl groups can be obtained from normally saturated sources and mixed with unsaturated acyl groups. In some useful mixtures of acyl groups, no more than 10% of unsaturated $C_{18}$ acyl groups are hydrogenated to their saturated counterparts. For some products, hydrogenation of diunsaturated and triunsaturated $C_{18}$ acyl groups is preferably maximized, consistent with minimal formation of saturated $C_{18}$ groups. For instance, triunsaturated acyl groups can be completely hydrogenated without achieving complete hydrogenation of diunsaturated acyl groups.

Hydrogenation of the triglyceride starting product which maximizes monounsaturated acyl groups can be readily achieved by maintaining an appropriate balance of the conditions of the hydrogenation reaction. The process variables in the hydrogenation of triglycerides and the effects of altering such variables, are generally quite familiar to those of ordinary skill in this art. In general, hydrogenation of the triglyceride starting product can be carried out at a temperature ranging (broadly stated) between 170° C. and 205° C. and more preferably within a somewhat narrower range of from 185° C. to 195° C. The other significant process variable is the pressure of hydrogen within the hydrogenation reactor. In general, this pressure should be maintained within a range (broadly stated) of from 2 psig to 20 psig, and more preferably between from 5 psig and 15 psig.

Within these ranges of parameters, hydrogenation can be carried out with a particular view to the effects of these parameters. Lower hydrogen pressures in the reactor permit a greater degree of control of the reaction, particularly as to its selectivity. By "selectivity" is meant the hydrogenation of diunsaturated and triunsaturated acyl groups without excessive hydrogenation of mono unsaturated acyl groups. On the other hand, higher hydrogen pressures afford less selectivity. Selectivity can be desirable in certain instances.

Higher hydrogenation temperatures are associated with faster rates of hydrogenation and with greater selectivity of the hydrogenation. Conversely, lower hydrogenation temperatures are associated with less selectivity (i.e. increased hydrogenation of the mono unsaturated groups), and particularly with slower hydrogenation rates in general.

These considerations are also balanced with considerations of stereochemistry. More specifically, the presence of unsaturation in the acyl groups can lead to the formation of different stereoisomers in the acyl groups upon hydrogenation. The two possible stereoisomeric configurations for unsaturated fatty acyl groups are known as the "cis" and the "trans" forms. The presence of the cis form is preferred, as it is associated with a lower melting point of the eventual product and, thus with greater fluidity, and better low temperature phase stability of clear compositions. Thus, another reason that canola oil is a particularly preferred triglyceride starting product is that, as a naturally occurring material, the acyl groups present in this triglyceride exhibit only the cis form. In the hydrogenation, higher hydrogen pressures are associated also with a decreased tendency of the acyl group to undergo configuration change from the cis form to the trans form. Also, higher hydrogenation temperatures while favorable for some reasons are also associated with higher conversion of cis unsaturation to the trans form. Products exhibiting satisfactory properties can be obtained by appropriate control of the hydrogenation conditions so as to afford both selectivity and control of the stereochemical configurations of the product.

The hydrogenation is carried out in the presence of a suitable hydrogenation catalyst. Such catalysts are well known and commercially available. They generally comprise nickel, palladium, ruthenium or platinum, typically on a suitable catalyst support. A suitable catalyst is a nickel based catalyst such as sold by Engelhard under the trade designation "N-545"®.

In one variation, the hydrogenation is carried out to an end point at which hydrogenation of the diunsaturation and triunsaturation in the triglyceride product is maximized, while formation of saturated acyl groups is minimized. The progress of the hydrogenation reaction toward the end point can readily be monitored by periodic measurement of the iodine value of the reaction mass. As the hydrogenation proceeds, the Iodine Value decreases. For example, the hydrogenation reaction can be discontinued when the Iodine Value reaches 95.

Other requirements for hydrogenation reactions are well known, such as the types of reactor, cooling means to maintain the desired temperature, the provision of means for agitation effective to provide adequate contact between the triglyceride and the hydrogen and catalyst, etc.

The triglyceride containing the desired acyl groups is reacted, typically by hydrolyzing or transesterification, to obtain the desired fatty acyl groups as, e.g., the corresponding fatty acids and/or fatty acid esters. That is, the three ester bonds in the triglyceride are broken so that the hydrogenated combination of acyl groups is converted to a mixtures of fatty acids and/or esters having the same chain length distribution as in the acyl groups, and having the distribution of saturation and unsaturation provided by the hydrogenation reaction.

Hydrolysis can be carried out under any of the suitable conditions known in this art for hydrolysis of triglycerides into their fatty acid constituents. In general, the triglyceride is reacted with high temperature steam in a reactor, wherein the fatty acids are split off from glycerine, following which the steam is condensed to form an aqueous solution of glycerine and this solution is removed. Transesterification of the triglyceride can be carried out under any of the suitable conditions known in this art for transesterification of triglycerides into their fatty acid ester constituents.

Once the fatty acid fraction is obtained, according to step a) of the invention process, it is reacted (or also called esterified) with triethanolamine for a period such that the condensation product obtained compound has an acid value (AV), measured by measured by titration of the condensation product with a standard KOH solution against a phenolphtaleine indicator according to ISO#53402, of less than 6.5.

For optimum softness benefit, it is preferred that the reactants are present in a molar ratio of fatty acid to triethanolamine of from 1:1 to 2.5:1. More preferably, the reactants are present in a molar ratio of fatty acid fraction to triethanolamine of from 1.4:1 to less than 1.8:1, preferably 1.5:1 when the aqueous medium in which they are to be used comprises a molar ratio of anionic surfactant to said softener compound of the invention of at least 1:10.

On the other hand, when the aqueous medium in which they are to be used comprises a molar ratio of anionic surfactant to said softener compound of the invention of less than 1:10, the reactants are preferably present in a molar ratio of fatty acid fraction to triethanolamine of from 1.8:1 to 2.2:1, preferably 2.0:1.

The esterification is carried out under conventional esterification conditions, providing an acidic catalyst and providing for withdrawal of byproduct water of condensation. Preferably, a small amount generally up to 1.0 wt. % of the reactant (i.e. acids and amine), of hypo phosphorous acid (HPPA) is added to the esterification reaction mixture. The HPPA is believed to catalyze the reaction and as well to preserve or even improve the color of the product obtained in this reaction. Indeed, color control is critical to the appearance of clear softening compositions. Preferably, esterification is allowed to proceed completely such that all amine present is esterified with the fatty acid fraction. The Av is measured at different time interval on the esterified reaction product and the condensation reaction (also called esterification reaction) is not stopped until the required AV is reached. This AV determination is made according to the ISO defined herein before.

After the required acid value for the condensation product has been obtained, it is, according to step b) of the invention process, reacted with an alkylating agent, in the presence or absence of a solvent.

The alkylation (also called quaternisation step) is carried out under conditions and with reactants generally familiar to those experienced in this field. The quaternizing agent has the formula QA, wherein Q is preferably methyl, benzyl, or ethyl, and A is an inert monovalent anion.

Preferably, the alkylating agent is selected from alkyl halides, sulphates, phosphates and carbonates, more preferably alkyl halides and sulphates. Suitable alkyl halide compounds for use as alkylating agents in the present invention are selected from methyl chloride, benzyl chloride.

Suitable alkyl sulphate compounds for use as alkylating agents in the present invention are the polyalkylsulphates selected from dimethylsulphate and diethylsulphate. One of the more preferred alkylating agent is dimethylsulfate.

This alkylation step produces the quaternary ammonium ester of the invention.

When the softener compound of the invention is formulated into clear or translucent compositions, it is most preferred to drive the quaternising reaction as far to completion as possible, for the best clarity of the finished composition. This is most particularly desirable when a high perfume level in the composition is present, e.g of more than 1.5% by weight of the composition of perfume and typically of 2.5% by weight. Such completion reaction can typically be done though longer reaction times, controlling temperatures and pressures, and using excess alkylating agent in the reaction. It is also most preferred to remove unreacted alkylating agent upon completion of the reaction to avoid malodor and also potential safety issues (e.g. methyl chloride may be removed by vacuum stripping).

C-Fabric Softening Composition

The compound of the invention is preferably incorporated in a fabric softening composition. Typical levels of incorporation are of from 1% to 80% by weight, preferably from 5% to 75%, more preferably from 15% to 70%, and even more preferably from 19% to 65%, by weight of the composition. Of course, mixtures of the above defined compound can be used herein. The softening composition according to the present invention can be in different form such as in liquid or solid form as defined hereinafter.

When formulated as a liquid fabric softening composition, the composition may be in the form of a dispersion, e.g. aqueous dispersion, or also in the form of a clear composition. Accordingly, when in liquid form, the composition in addition to the softening compound of the invention will also preferably comprises optional ingredients. When in such liquid forms, it has been found most preferred, in order to improve the stability of the softening composition according to the invention, that the softening compositions have a pH of from 3 to 4.

III. Optional Ingredients (A)-Principal Solvent

A principal solvent is one of the preferred optional ingredient for use in the present composition invention. The compositions of the present invention may comprise a principal solvent system. This is particularly the case when formulating liquid, clear fabric softening compositions. When employed, the principal solvent is typically used at a level of less than 40% by weight, preferably from 6% to 35%, more preferably from 8% to 25%, and even more preferably from 10% to 20%, by weight of the composition. The principal solvent is selected to minimize solvent odor impact in the composition and to provide a low viscosity to the final composition. For example, isopropyl alcohol is not very effective and has a strong odor. n-Propyl alcohol is more effective, but also has a distinct odor. Several butyl alcohols also have odors but can be used for effective clarity/stability, especially when used as part of a principal solvent system to minimize their odor. The alcohols are also selected for optimum low temperature stability, that is they are able to form compositions that are liquid with acceptable low viscosities and translucent, preferably clear, down to about 40° F. (about 4.4° C.) and are able to recover after storage down to about 20° F. (about 6.7° C.).

The suitability of any principal solvent for the formulation of the liquid, concentrated, preferably clear, fabric softener compositions herein with the requisite stability is surprisingly selective. Suitable solvents can be selected based upon their octanol/water partition coefficient (P). Octanol/water partition coefficient of a principal solvent is the ratio between its equilibrium concentration in octanol and in water. The partition coefficients of the principal solvent ingredients of this invention are conveniently given in the form of their logarithm to the base 10, logP.

The logP of many ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database.

The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each ingredient, and takes into account the numbers and types of atoms, the atom connectivity, and chemical bonding. These ClogP values, which are the most reliable and widely used estimates for this physicochemical property, are preferably used instead of the experimental logP values in the selection of the principal solvent ingredients which are useful in the present invention. Other methods that can be used to compute ClogP include, e.g., Crippen's fragmentation method as disclosed in J. Chem. Inf. Comput. Sci., 27, 21 (1987); Viswanadhan's fragmentation method as disclose in J. Chem. Inf. Comput. Sci., 29, 163 (1989); and Broto's method as disclosed in Eur. J. Med. Chem.—Chim. Theor., 19, 71 (1984). The principal solvents herein are selected from those having a ClogP of from about 0.15 to about 0.64, preferably from about 0.25 to about 0.62, and more preferably from about 0.40 to about 0.60, said principal solvent preferably being at least somewhat asymmetric, and preferably having a melting, or solidification, point that allows it to be liquid at, or near room temperature. Solvents that have a low molecular weight and are biodegradable are also desirable for some purposes. The more assymetric solvents appear to be very desirable, whereas the highly symmetrical solvents such as 1,7-heptanediol, or 1,4-bis(hydroxymethyl) cyclohexane, which have a center of symmetry, appear to be unable to provide the essential clear compositions when used alone, even though their ClogP values fall in the preferred range.

The most preferred principal solvents can be identified by the appearance of the softener vesicles, as observed via cryogenic electron microscopy of the compositions that have been diluted to the concentration used in the rinse. These dilute compositions appear to have dispersions of fabric softener that exhibit a more unilamellar appearance than conventional fabric softener compositions. The closer to uni-lamellar the appearance, the better the compositions seem to perform. These compositions provide surprisingly good fabric softening as compared to similar compositions prepared in the conventional way with the same fabric softener active.

Operable principal solvents are disclosed and listed below which have ClogP values which fall within the requisite range. These include mono-ols, C6 diols, C7 diols, octanediol isomers, butanediol derivatives, trimethylpentanediol isomers, ethylmethylpentanediol isomers, propyl pentanediol isomers, dimethylhexanediol isomers, ethylhexanediol isomers, methylheptanediol isomers, octanediol isomers, nonanediol isomers, alkyl glyceryl ethers, di(hydroxy alkyl) ethers, and aryl glyceryl ethers, aromatic glyceryl ethers, alicyclic diols and derivatives, $C_3C_7$ diol alkoxylated derivatives, aromatic diols, and unsaturated diols. These principal solvents are all disclosed in WO 97/03169 having the title "CONCENTRATED, STABLE, PREFERABLY CLEAR, FABRIC SOFTENING COMPOSITION".

Particularly preferred principal solvents include hexanediols such as 1,2-hexanediol; and C8 diols such as 2-ethyl-1,3-hexanediol and 2,2,4-trimethyl-1,3-pentanediol, ethoxylates of 2,2,4-trimethyl-1,3-pentanediol and ethoxylates of 2-ethyl-1,3-hexanediol; and 1,2 cyclohexanedimethanol.

Mixtures of principal solvent can also be used for the purpose of the present invention.

The principal solvents are desirably kept to the lowest levels that are feasible in the present compositions for obtaining translucency or clarity. The presence of water exerts an important effect on the need for the principal solvents to achieve clarity of these compositions. The higher the water content, the higher the principal solvent level (relative to the softener level) is needed to attain product clarity. Inversely, the less the water content, the less principal solvent (relative to the softener) is needed. Thus, at low water levels of from 5% to 15%, the softener active-to-principal solvent weight ratio is preferably from 55:45 to 85:15, more preferably from 60:40 to 80:20. At water levels of from 15% to 70%, the softener active-to-principal solvent weight ratio is preferably from 45:55 to 70:30, more preferably from 55:45 to 70:30. But at high water levels of from 70% to 80%, the softener active-to-principal solvent weight ratio is preferably from 30:70 to 55:45, more preferably from 35:65 to 45:55. At even higher water levels, the softener to principal solvent ratios should also be even higher.

The compositions can also inherently provide improved perfume deposition of certain perfume components, especially for those that are poorly fabric substantive as compared to conventional fabric softening compositions, especially when the perfume is added to the compositions at, or near, room temperature.

More preferred for use herein is a combination of principal solvents. Most preferred combinations are 2,2,4-trimethyl-1,3-pentanediol (TMPD) in combination with 1,2 hexanediol. With the above preferred combinations, lower total levels of solvents can be achieved thereby reducing the overall cost of the formulation. By the present principal solvent combinations, it has been found that the resulting products have surprising phase stability and fully recover from freezing down to 0° F. (−18° C.). The resulting products have also been surprisingly found to have excellent water dispersibility. Furthermore, another advantage with the use of such combination is their large availibility.

(B)

Low molecular weight water soluble solvents can also be used at levels of from 0% to 12%, preferably from 1% to 10%, more preferably from 2% to 8% by weight. The water soluble solvents cannot provide a clear product at the same low levels of the principal solvents described hereinbefore but can provide clear product when the principal solvent is not sufficient to provide completely clear product. The presence of these water soluble solvents is therefore highly desirable. Such solvents include: ethanol; isopropanol; 1,2-propanediol; 1,3-propanediol; propylene carbonate; 1,4-cyclohexanedimethanol; etc. but do not include any of the principal solvents (A). These water soluble solvents have a greater affinity for water in the presence of hydrophobic materials like the softener compound than the principal solvents.

Among the above described co-solvent to be used in combination with the principal solvent, 1,4 cyclohexanedimethanol is a preferred co-solvent.

(C) Brighteners

The compositions herein can also optionally contain from 0.005% to 5% by weight of certain types of hydrophilic optical brighteners which also provide a dye transfer inhibition action. If used, the compositions herein will preferably comprise from 0.001% to 1% by weight of such optical brighteners.

The hydrophilic optical brighteners useful in the present invention are those having the structural formula:

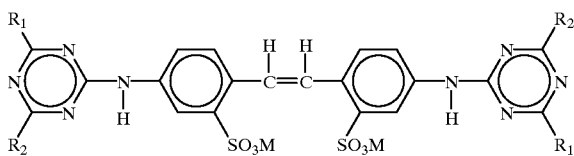

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX® by Ciba-Geigy Corporation. Tinopal-UNPA-GX is the preferred hydrophilic optical brightener useful in the rinse added compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX® by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX® by Ciba Geigy Corporation.

(D) Dispersibility Aids

Relatively concentrated compositions containing both saturated and unsaturated diester quaternary ammonium compounds can be prepared that are stable without the addition of concentration aids. However, the compositions of the present invention may require organic and/or inorganic concentration aids to go to even higher concentrations and/or to meet higher stability standards depending on the other ingredients. These concentration aids which typically can be viscosity modifiers may be needed, or preferred, for ensuring stability under extreme conditions when particular softener active levels are used. The surfactant concentration aids are typically selected from the group consisting of (1) single long chain alkyl cationic surfactants; (2) nonionic surfactants; (3) amine oxides; (4) fatty acids; and (5) mixtures thereof. These aids are described in P&G Copending Application Ser. No. 08/461,207, filed Jun. 5, 1995, Wahl et al., specifically on page 14, line 12 to page 20, line 12, which is herein incorporated by reference. When said dispersibility aids are present, the total level is from 2% to 25%, preferably from 3% to 17%, more preferably from 4% to 15%, and even more preferably from 5% to 13% by weight of the composition. These materials can either be added as part of the active softener raw material, (I), e.g., the mono-long chain alkyl cationic surfactant and/or the fatty acid which are reactants used to form the biodegradable fabric softener active as discussed hereinbefore, or added as a separate component. The total level of dispersibility aid includes any amount that may be present as part of component (I).

(1) Mono-Alkyl Cationic Quaternary Ammonium Compound

When the mono-alkyl cationic quaternary ammonium compound is present, it is typically present at a level of from 2% to 25%, preferably from 3% to 17%, more preferably from 4% to 15%, and even more preferably from 5% to 13% by weight of the composition, the total mono-alkyl cationic quaternary ammonium compound being at least at an effective level.

Such mono-alkyl cationic quaternary ammonium compounds useful in the present invention are, preferably, quaternary ammonium salts of the general formula:

$$[R^4N+(R^5)_3]X^-$$

wherein $R^4$ is $C_8$–$C_{22}$ alkyl or alkenyl group, preferably $C_{10}$–$C_{18}$ alkyl or alkenyl group; more preferably $C_{10}$–$C_{14}$ or $C_{16}$–$C_{18}$ alkyl or alkenyl group;

each $R^5$ is a $C_1$–$C_6$ alkyl or substituted alkyl group (e.g., hydroxy alkyl), preferably $C_1$–$C_3$ alkyl group, e.g., methyl (most preferred), ethyl, propyl, and the like, a benzyl group, hydrogen, a polyethoxylated chain with from 2 to 20 oxyethylene units, preferably from 2.5 to 13 oxyethylene units, more preferably from 3 to 10 oxyethylene units, and mixtures thereof; and $X^-$ is as defined hereinbefore for (Formula (I)).

Especially preferred dispersibility aids are monolauryl trimethyl ammonium chloride and monotallow trimethyl ammonium chloride available from Witco under the trade names Adogen® 412 and Adogen® 471, monooleyl or monocanola trimethyl ammonium chloride available from Witco under the tradename Adogen® 417, monococonut trimethyl ammonium chloride available from Witco under the trade name Adogen® 461, and monosoya trimethyl ammonium chloride available from Witco under the trade name Adogen® 415.

The $R^4$ group can also be attached to the cationic nitrogen atom through a group containing one, or more, ester, amide, ether, amine, etc., linking groups which can be desirable for increased concentratability of component (I), etc. Such linking groups are preferably within from one to three carbon atoms of the nitrogen atom.

Mono-alkyl cationic quaternary ammonium compounds also include $C_8$–$C_{22}$ alkyl choline esters. The preferred dispersibility aids of this type have the formula:

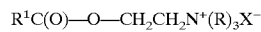

wherein $R^1$, R and $X^-$ are as defined previously.

Highly preferred dispersibility aids include $C_{12}$–$C_{14}$ coco choline ester and $C_{16}$–$C_{18}$ tallow choline ester.

Suitable biodegradable single-long-chain alkyl dispersibility aids containing an ester linkage in the long chains are described in U.S. Pat. No. 4,840,738, Hardy and Walley, issued Jun. 20, 1989, said patent being incorporated herein by reference.

When the dispersibility aid comprises alkyl choline esters, preferably the compositions also contain a small amount, preferably from 2% to 5% by weight of the composition, of organic acid. Organic acids are described in European Patent Application No. 404,471, Machin et al., published on Dec. 27, 1990, supra, which is herein incorporated by reference. Preferably the organic acid is selected from the group consisting of glycolic acid, acetic acid, citric acid, and mixtures thereof.

Ethoxylated quaternary ammonium compounds which can serve as the dispersibility aid include ethylbis (polyethoxy ethanol)alkylammonium ethyl-sulfate with 17 moles of ethylene oxide, available under the trade name Variquat® 66 from Witco Corporation; polyethylene glycol (15) oleammonium chloride, available under the trade name Ethoquad® O/25 from Akzo; and polyethylene glycol (15) cocomonium chloride, available under the trade name Ethoquad® C/25 from Akzo.

Quaternary compounds having only a single long alkyl chain, can protect the cationic softener from interacting with anionic surfactants and/or detergent builders that are carried over into the rinse from the wash solution.

(2) Nonionic Surfactant (Alkoxylated Materials)

Suitable nonionic surfactants to serve as the viscosity/dispersibility modifier include addition products of ethylene oxide and, optionally, propylene oxide, with fatty alcohols, fatty acids, fatty amines, etc. They are referred to herein as ethoxylated fatty alcohols, ethoxylated fatty acids, and ethoxylated fatty amines.

Any of the alkoxylated materials of the particular type described hereinafter can be used as the nonionic surfactant. In general terms, the nonionics herein, when used alone, in liquid compositions are at a level of from 0% to 5%, preferably from 0.1% to 5%, more preferably from 0.2% to 3%. Suitable compounds are substantially water-soluble surfactants of the general formula:

$$R^2-Y-(C_2H_4O)_z-C_2H_4OH$$

wherein $R^2$ for both solid and liquid compositions is selected from the group consisting of primary, secondary and branched chain alkyl and/or acyl hydrocarbyl groups; primary, secondary and branched chain alkenyl hydrocarbyl groups; and primary, secondary and branched chain alkyl- and alkenyl-substituted phenolic hydrocarbyl groups; said hydrocarbyl groups having a hydrocarbyl chain length of from 8 to 20, preferably from 10 to 18 carbon atoms. More preferably the hydrocarbyl chain length for liquid compositions is from 16 to 18 carbon atoms and for solid compositions from 10 to 14 carbon atoms. In the general formula for the ethoxylated nonionic surfactants herein, Y is typically —O—, —C(O)O—, —C(O)N(R)—, or —C(O)N(R)R—, preferably —O—, and in which $R^2$, and R, when present, have the meanings given hereinbefore, and/or R can be hydrogen, and z is at least 8, preferably at least 10–11. Performance and, usually, stability of the softener composition decrease when fewer ethoxylate groups are present.

The nonionic surfactants herein are characterized by an HLB (hydrophilic-lipophilic balance) of from 7 to 20, preferably from 8 to 15. Of course, by defining $R^2$ and the number of ethoxylate groups, the HLB of the surfactant is, in general, determined. However, it is to be noted that the nonionic ethoxylated surfactants useful herein, for concentrated liquid compositions, contain relatively long chain $R^2$ groups and are relatively highly ethoxylated. While shorter alkyl chain surfactants having short ethoxylated groups can possess the requisite HLB, they are not as effective herein.

Nonionic surfactants as the viscosity/dispersibility modifiers are preferred over the other modifiers disclosed herein for compositions with higher levels of perfume.

Examples of nonionic surfactants follow. The nonionic surfactants of this invention are not limited to these examples. In the examples, the integer defines the number of ethoxy (EO) groups in the molecule.

(3) Amine Oxides

Suitable amine oxides include those with one alkyl or hydroxyalkyl moiety of 8 to 22 carbon atoms, preferably from 10 to 18 carbon atoms, more preferably from 8 to 14 carbon atoms, and two alkyl moieties selected from the group consisting of alkyl groups and hydroxyalkyl groups with 1 to 3 carbon atoms.

Examples include dimethyloctylamine oxide, diethyldecylamine oxide, bis-2-hydroxyethyl)dodecyl-amine oxide, dimethyldodecylamine oxide, dipropyl-tetradecylamine oxide, methylethylhexadecylamine oxide, dimethyl-2-hydroxyoctadecylamine oxide, and coconut fatty alkyl dimethylamine oxide.

(E) Stabilizers

Stabilizers can be present in the compositions of the present invention. The term "stabilizer," as used herein, includes antioxidants and reductive agents. These agents are present at a level of from 0% to 2%, preferably from 0.01% to 0.2%, more preferably from 0.035% to 0.1% for antioxidants, and more preferably from 0.01% to 0.2% for reductive agents. These assure good odor stability under long term storage conditions. Antioxidants and reductive agent stabilizers are especially critical for unscented or low scent products (no or low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox® S-1; a mixture of BHT (butylated hydroxytoluene), BHA (butylated hydroxyanisole), propyl gallate, and citric acid, available from Eastman Chemical Products, Inc., under the trade name Tenox®-6; butylated hydroxytoluene, available from UOP Process Division under the trade name Sustane® BHT; tertiary butylhydroquinone, Eastman Chemical Products, Inc., as Tenox® TBHQ; natural tocopherols, Eastman Chemical Products, Inc., as Tenox® GT-1/GT-2; and butylated hydroxyanisole, Eastman Chemical Products, Inc., as BHA; long chain esters ($C_8$–$C_{22}$) of gallic acid, e.g., dodecyl gallate; Irganox® 1010; Irganox® 1035; Irganox® B 1171; Irganox® 1425; Irganox® 3114; Irganox® 3125; and mixtures thereof; preferably Irganox®3125, Irganox® 1425, Irganox® 3114, and mixtures thereof; more preferably Irganox® 3125 alone or mixed with citric acid and/or other chelators such as isopropyl citrate, Dequest® 2010, available from Monsanto with a chemical name of 1-hydroxyethylidene-1, 1-diphosphonic acid (etidronic acid), and Tiron®, available from Kodak with a chemical name of 4,5-dihydroxy-m-benzene-sulfonic acid/sodium salt, and DTPA®, available from Aldrich with a chemical name of diethylenetriaminepentaacetic acid.

(F) Soil Release Agent

In the present invention, an optional soil release agent can be added. The addition of the soil release agent can occur in combination with the premix, in combination with the acid/water seat, before or after electrolyte addition, or after the final composition is made. The softening composition prepared by the process of the present invention herein can contain from 0% to 10%, preferably from 0.2% to 5%, of a soil release agent. Preferably, such a soil release agent is a polymer. Polymeric soil release agents useful in the present invention include copolymeric blocks of terephthalate and polyethylene oxide or polypropylene oxide, and the like.

A preferred soil release agent is a copolymer having blocks of terephthalate and polyethylene oxide. More specifically, these polymers are comprised of repeating units of ethylene terephthalate and polyethylene oxide terephthalate at a molar ratio of ethylene terephthalate units to polyethylene oxide terephthalate units of from 25:75 to 35:65, said polyethylene oxide terephthalate containing polyethylene oxide blocks having molecular weights of from 300 to 2000. The molecular weight of this polymeric soil release agent is in the range of from 5,000 to 55,000.

Another preferred polymeric soil release agent is a crystallizable polyester with repeat units of ethylene terephthalate units containing from 10% to 15% by weight of ethylene terephthalate units together with from 10% to 50% by weight of polyoxyethylene terephthalate units, derived from a polyoxyethylene glycol of average molecular weight of from 300 to 6,000, and the molar ratio of ethylene terephthalate units to polyoxyethylene terephthalate units in the crystallizable polymeric compound is between 2:1 and 6:1. Examples of this polymer include the commercially available materials Zelcon 4780® (from Dupont) and Milease T® (from ICI).

Highly preferred soil release agents are polymers of the generic formula:

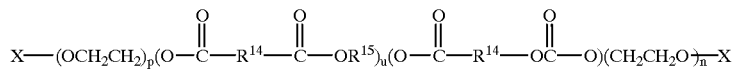

in which each X can be a suitable capping group, with each X typically being selected from the group consisting of H, and alkyl or acyl groups containing from 1 to 4 carbon atoms. p is selected for water solubility and generally is from 6 to 113, preferably from 20 to 50. u is critical to formulation in a liquid composition having a relatively high ionic strength. There should be very little material in which u is greater than 10. Furthermore, there should be at least 20%, preferably at least 40%, of material in which u ranges from 3 to 5.

The $R^{14}$ moieties are essentially 1,4-phenylene moieties. As used herein, the term "the $R^{14}$ moieties are essentially 1,4-phenylene moieties" refers to compounds where the $R^{14}$ moieties consist entirely of 1,4-phenylene moieties, or are partially substituted with other arylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphthylene, 1,4-naphthylene, 2,2-biphenylene, 4,4-biphenylene, and mixtures thereof. Alkylene and alkenylene moieties which can be partially substituted include 1,2-propylene, 1,4-butylene, 1,5-pentylene, 1,6-hexamethylene, 1,7-heptamethylene, 1,8-octamethylene, 1,4-cyclohexylene, and mixtures thereof.

For the $R^{14}$ moieties, the degree of partial substitution with moieties other than 1,4-phenylene should be such that the soil release properties of the compound are not adversely affected to any great extent. Generally the degree of partial substitution which can be tolerated will depend upon the backbone length of the compound, i.e., longer backbones can have greater partial substitution for 1,4-phenylene moieties. Usually, compounds where the $R^{14}$ comprise from 50% to 100% 1,4-phenylene moieties (from 0% to 50% moieties other than 1,4-phenylene) have adequate soil release activity. For example, polyesters made according to the present invention with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $R^{14}$ moieties consist entirely of (i.e., comprise 100%) 1,4-phenylene moieties, i.e., each $R^{14}$ moiety is 1,4-phenylene.

For the $R^{15}$ moieties, suitable ethylene or substituted ethylene moieties include ethylene, 1,2-propylene, 1,2-butylene, 1,2-hexylene, 3-methoxy-1,2-propylene, and mixtures thereof. Preferably, the $R^{15}$ moieties are essentially ethylene moieties, 1,2-propylene moieties, or mixtures thereof. Inclusion of a greater percentage of ethylene moieties tends to improve the soil release activity of compounds. Surprisingly, inclusion of a greater percentage of 1,2-propylene moieties tends to improve the water solubility of compounds.

Therefore, the use of 1,2-propylene moieties or a similar branched equivalent is desirable for incorporation of any substantial part of the soil release component in the liquid fabric softener compositions. Preferably, from 75% to 100%, are 1,2-propylene moieties.

The value for each p is at least 6, and preferably is at least 10. The value for each n usually ranges from 12 to 113. Typically the value for each p is in the range of from 12 to 43.

A more complete disclosure of soil release agents is contained in U.S. Pat. Nos.: 4,661,267; 4,711,730; 4,749,596; 4,818,569; 4,877,896; 4,956,447; and 4,976,879, all of said patents being incorporated herein by reference.

These soil release agents can also act as scum dispersants.

(G) Scum Dispersant

In the present invention, the premix can be combined with an optional scum dispersant, other than the soil release agent, and heated to a temperature at or above the melting point(s) of the components.

The preferred scum dispersants herein are formed by highly ethoxylating hydrophobic materials. The hydrophobic material can be a fatty alcohol, fatty acid, fatty amine, fatty acid amide, amine oxide, quaternary ammonium compound, or the hydrophobic moieties used to form soil release polymers. The preferred scum dispersants are highly ethoxylated, e.g., more than 17, preferably more than 25, more preferably more than 40, moles of ethylene oxide per molecule on the average, with the polyethylene oxide portion being from 76% to 97%, preferably from 81% to 94%, of the total molecular weight.

The level of scum dispersant is sufficient to keep the scum at an acceptable, preferably unnoticeable to the consumer, level under the conditions of use, but not enough to adversely affect softening. For some purposes it is desirable that the scum is nonexistent. Depending on the amount of anionic or nonionic detergent, etc., used in the wash cycle of a typical laundering process, the efficiency of the rinsing steps prior to the introduction of the compositions herein, and the water hardness, the amount of anionic or nonionic detergent surfactant and detergency builder (especially phosphates and zeolites) entrapped in the fabric (laundry) will vary. Normally, the minimum amount of scum dispersant should be used to avoid adversely affecting softening properties. Typically scum dispersion requires at least 2%, preferably at least 4% (at least 6% and preferably at least 10% for maximum scum avoidance) based upon the level of softener active. However, at levels of 10% (relative to the softener material) or more, one risks loss of softening efficacy of the product especially when the fabrics contain high proportions of nonionic surfactant which has been absorbed during the washing operation.

Preferred scum dispersants are: Brij 700®; Varonic U-250®; Genapol T-500®) Genapol T-800®; Plurafac A-79®; and Neodol 25-50®.

(H) Bactericides

Examples of bactericides used in the compositions of this invention include glutaraldehyde, formaldehyde, 2-bromo-2-nitro-propane-1,3-diol sold by Inolex Chemicals, located in Philadelphia, Pa., under the trade name Bronopol®, and a mixture of 5-chloro-2-methyl-4-isothiazoline-3-one and 2-methyl-4-isothiazoline-3-one sold by Rohm and Haas Company under the trade name Kathon 1 to 1,000 ppm by weight of the agent.

(I) Perfume

The present invention can contain any softener compatible perfume. Suitable perfumes are disclosed in U.S. Pat. No. 5,500,138, said patent being incorporated herein by reference.

As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

Examples of perfume ingredients useful in the perfumes of the present invention compositions include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma.

Additional examples of fragrance materials include, but are not limited to, orange oil; lemon oil; grapefruit oil; bergamot oil; clove oil; dodecalactone gamma; methyl-2-(2-pentyl-3-oxo-cyclopentyl) acetate; beta-naphthol methylether; methyl-beta-naphthylketone; coumarin; decylaldehyde; benzaldehyde; 4-tert-butylcyclohexyl acetate; alpha, alpha-dimethylphenethyl acetate; methylphenylcarbinyl acetate; Schiff's base of 4-(4-hydroxy-4-methylpentyl)-3-cyclohexene-1-carboxaldehyde and methyl anthranilate; cyclic ethyleneglycol diester of tridecandioic acid; 3,7-dimethyl-2,6-octadiene-1-nitrile; ionone gamma methyl; ionone alpha; ionone beta; petitgrain; methyl cedrylone; 7-acetyl-1,2,3,4,5,6,7,8-octahydro-1,1,6,7-tetramethyl-naphthalene; ionone methyl; methyl-1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; benzophenone; 6-acetyl-1,1,2,3,3,5-hexamethyl indane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; ambroxane; dodecahydro-3a,6,6,9a-tetramethylnaphtho-[2,1b]furan; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; and condensation products of: hydroxycitronellal and methyl anthranilate; hydroxycitronellal and indol; phenyl acetaldehyde and indol; 4-(4-hydroxy-4-methyl pentyl)-3-cyclohexene-1-carboxaldehyde and methyl anthranilate.

More examples of perfume components are geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; ethylene brassylate.

The perfumes useful in the present invention compositions are substantially free of halogenated materials and nitromusks.

Suitable solvents, diluents or carriers for perfumes ingredients mentioned above are for examples, ethanol, isopropanol, diethylene glycol, monoethyl ether, dipropylene glycol, diethyl phthalate, triethyl citrate, etc. The amount of such solvents, diluents or carriers incorporated in the perfumes is preferably kept to the minimum needed to provide a homogeneous perfume solution.

Perfume can be present at a level of from 0% to 10%, preferably from 0.1% to 5%, and more preferably from 0.2% to 3%, by weight of the finished composition. Fabric softener compositions of the present invention provide improved fabric perfume deposition.

(J) Chelating Agents

The compositions and processes herein can optionally employ one or more copper and/or nickel chelating agents ("chelators"). Such water-soluble chelating agents can be selected from the group consisting of amino carboxylates, amino phosphonates, polyfunctionally-substituted aromatic chelating agents and mixtures thereof, all as hereinafter defined. The whiteness and/or brightness of fabrics are substantially improved or restored by such chelating agents and the stability of the materials in the compositions are improved.

Amino carboxylates useful as chelating agents herein include ethylenediaminetetraacetates (EDTA), N-hydroxyethylethylenediaminetriacetates, nitrilotriacetates (NTA), ethylenediamine tetraproprionates, ethylenediamine-N,N'-diglutamates, 2-hyroxypropylenediamine-N,N'-disuccinates, triethylenetetraaminehexacetates, diethylenetriaminepentaacetates (DETPA), and ethanoldiglycines, including their water-soluble salts such as the alkali metal, ammonium, and substituted ammonium salts thereof and mixtures thereof.

Amino phosphonates are also suitable for use as chelating agents in the compositions of the invention when at least low levels of total phosphorus are permitted in detergent compositions, and include ethylenediaminetetrakis (methylenephosphonates), diethylenetriamine-N,N,N',N",N"-pentakis(methane phosphonate) (DETMP) and 1-hydroxyethane-1,1-diphosphonate (HEDP). Preferably, these amino phosphonates to not contain alkyl or alkenyl groups with more than 6 carbon atoms.

The chelating agents are typically used in the present rinse process at levels from 2 ppm to 25 ppm, for periods from 1 minute up to several hours' soaking.

The preferred EDDS chelator used herein (also known as ethylenediamine-N,N'-disuccinate) is the material described in U.S. Pat. No. 4,704,233, cited hereinabove, and has the formula (shown in free acid form):

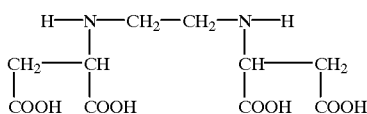

As disclosed in the patent, EDDS can be prepared using maleic anhydride and ethylenediamine. The preferred biodegradable [S,S] isomer of EDDS can be prepared by reacting L-aspartic acid with 1,2-dibromoethane. The EDDS has advantages over other chelators in that it is effective for chelating both copper and nickel cations, is available in a biodegradable form, and does not contain phosphorus. The EDDS employed herein as a chelator is typically in its salt form, i.e., wherein one or more of the four acidic hydrogens are replaced by a water-soluble cation M, such as sodium, potassium, ammonium, triethanolammonium, and the like. As noted before, the EDDS chelator is also typically used in the present rinse process at levels from 2 ppm to 25 ppm for periods from 1 minute up to several hours' soaking. At certain pH's the EDDS is preferably used in combination with zinc cations.

As can be seen from the foregoing, a wide variety of chelators can be used herein. Indeed, simple polycarboxylates such as citrate, oxydisuccinate, and the like, can also be used, although such chelators are not as effective as the amino carboxylates and phosphonates, on a weight basis. Accordingly, usage levels may be adjusted to take into account differing degrees of chelating effectiveness. The chelators herein will preferably have a stability constant (of the fully ionized chelator) for copper ions of at least 5, preferably at least 7. Typically, the chelators will comprise from 0.5% to 10%, more preferably from 0.75% to 5%, by weight of the compositions herein. Preferred chelators include DETMP, DETPA, NTA, EDDS and mixtures thereof.

(K)-Enzyme

The compositions and processes herein can optionally employ one or more enzymes such as lipases, proteases, cellulase, amylases and peroxidases. A preferred enzyme for use herein is a cellulase enzyme. Indeed, this type of enzyme will further provide a color care benefit to the treated fabric. Cellulases usable herein include both bacterial and fungal types, preferably having a pH optimum between 5 and 9.5. U.S. Pat. No. 4,435,307 discloses suitable fungal cellulases from *Humicola insolens* or Humicola strain DSM1800 or a cellulase 212—producing fungus belonging to the genus Aeromonas, and cellulase extracted from the hepatopancreas of a marine mollusk, Dolabella Auricula Solander. Suitable cellulases are also disclosed in GB-A-2.075.028; GB-A-2.095.275 and DE-OS-2.247.832. CAREZYME® and CELLUZYME® (Novo) are especially useful. Other suitable cellulases are also disclosed in WO 91/17243 to Novo, WO 96/34092, WO 96/34945 and EP-A-0,739,982. In practical terms for current commercial preparations, typical amounts are up to 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. In the particular cases where activity of the enzyme preparation can be defined otherwise such as with cellulases, corresponding activity units are preferred (e.g. CEVU or cellulase Equivalent Viscosity Units). For instance, the compositions of the present invention can contain cellulase enzymes at a level equivalent to an activity from about 0.5 to 1000 CEVU/gram of composition. Cellulase enzyme preparations used for the purpose of formulating the compositions of this invention typically have an activity comprised between 1,000 and 10,000 CEVU/gram in liquid form, around 1,000 CEVU/gram in solid form.

(L) Other Optional Ingredients

The present invention can include optional components conventionally used in textile treatment compositions, for example: colorants; preservatives; surfactants; anti-shrinkage agents; fabric crisping agents; spotting agents; germicides; fungicides; anti-oxidants such as butylated hydroxy toluene, anti-corrosion agents, and the like.

The present invention can also include other compatible ingredients, including those as disclosed in copending applications Ser. No. 08/372,068, filed Jan. 12, 1995, Rusche, et al.; Ser. No. 08/372,490, filed Jan. 12, 1995, Shaw, et al.; and Ser. No. 08/277,558, filed Jul. 19, 1994, Hartman, et al., incorporated herein by reference.

Fabric Softener Processing

Also within the scope of the present invention, is a process for preparing a premix composition and a fabric softener composition from the premix. According to another aspect of the invention, the premix composition comprises a fabric softener compound of the invention and an effective amount of a component selected from the group consisting of principal solvents, low molecular weight water soluble solvents, water soluble calcium salt, water soluble magnesium salt, perfume, and mixtures thereof.

The use of a principal solvent allows the preparation of premixes comprising the softener active (from 55% to 85%, preferably from 60% to 80%, more preferably from 65% to 75%, by weight of the premix); the principal solvent (from 10% to 30%, preferably from 13% to 25%, more preferably from 15% to 20%, by weight of the premix); and optionally, the water soluble solvent (from 5% to 20%, preferably from 5% to 17%, more preferably from 5% to 15%, by weight of the premix). These premixes contain the desired amount of fabric softening active and sufficient principal solvent and, optionally, solvent to give the premix the desired viscosity for the desired temperature range. Typical viscosities suitable for processing are less than 1000 cps, preferably less than 500 cps, more preferably less than 300 cps. Use of low temperatures improves safety, by minimizing solvent vaporization, minimizes the degradation and/or loss of materials such as the biodegradable fabric softener active, perfumes, etc., and reduces the need for heating, thus saving on the expenses for processing. The result is improved environmental impact and safety from the manufacturing operation.

Examples of premixes and processes using them include premixes which typically contain from 55% to 85%, preferably from 60% to 80%, more preferably from 65% to 75%, of fabric softener active as exemplified in the Examples, mixed with from 10% to 30%, preferably from 13% to 25%, more preferably from 15% to 20%, of principal solvent such as 1,2-hexanediol, and from 5% to 20%, preferably from 5% to 15%, of water soluble solvent like ethanol and/or isopropanol and/or hexylene glycol.

These premixes can be used to formulate fabric softening compositions in processes comprising the steps of:
1. Make premix of fabric softening active, 11% ethanol, and 17% principal solvent, let cool to ambient temperature.
2. Mix perfume in the premix.
3. Make up water seat of water and HCl at ambient temperature. Optionally add chelant and/or antioxidant.
4. Add premix to water under good agitation.
5. Trim with $CaCl_2$ solution to desired viscosity.
6. Add dye solution to get desired color.

Typically, the pH of the premix in water is adjusted to from 1.5 to 5. The diester quaternary fabric softening actives (DEQAs); the principal solvents and, optionally, the water soluble solvents, can be formulated as premixes which can be used to prepare fabric softening compositions.

Solid Compositions
1. Solid particulate compositions

As discussed hereinbefore, the invention also comprises solid particulate composition comprising:
(A) from 50% to 95%, preferably from 60% to 90%, of said biodegradable fabric softening active;
(B) optionally, from 0% to 30%, preferably from 3% to 15%, of dispersibility modifier; and
(D) from 0% to 10% of a pH modifier.

Optional pH Modifier

Since the biodegradable ester fabric softener actives are somewhat labile to hydrolysis, it is preferable to include optional pH modifiers in the solid particulate composition to which water is to be added, to form stable dilute or concentrated liquid softener compositions. Said stable liquid compositions should have a pH (neat) of from 2 to 5, preferably from 2 to 4.5, more preferably from 2 to 4, and most preferably from 3 to 4.

The pH can be adjusted by incorporating a solid, water soluble Bronsted acid. Examples of suitable Bronsted acids include inorganic mineral acids, such as boric acid, sodium bisulfate, potassium bisulfate, sodium phosphate monobasic, potassium phosphate monobasic, and mixtures thereof; organic acids, such as citric acid, fumaric acid, maleic acid, malic acid, tannic acid, gluconic acid, glutamic acid, tartaric acid, glycolic acid, chloroacetic acid, phenoxyacetic acid, 1,2,3,4-butane tetracarboxylic acid, benzene sulfonic acid, benzene phosphonic acid, ortho-toluene sulfonic acid, para-toluene sulfonic acid, phenol sulfonic acid, naphthalene sulfonic acid, oxalic acid, 1,2,4,5-pyromellitic acid, 1,2,4-trimellitic acid, adipic acid, benzoic acid, phenylacetic acid, salicylic acid, succinic acid, and mixtures thereof; and mixtures of mineral inorganic acids and organic acids. Preferred pH modifiers are citric acid, gluconic acid, tartaric acid, 1,2,3,4-butane tetracarboxylic acid, malic acid, and mixtures thereof.

Optionally, materials that can form solid clathrates such as cyclodextrins and/or zeolites, etc., can be used as adjuvants in the solid particulate composition as host carriers of concentrated liquid acids and/or anhydrides, such as acetic acid, HCl, sulfuric acid, phosphoric acid, nitric acid, carbonic acid, etc. An example of such solid clatherates is carbon dioxide adsorbed in zeolite A, as disclosed in U.S. Pat. No. 3,888,998 and U.S. Pat. No. 4,007,134 both of said patents being incorporated herein by reference. Examples of inclusion complexes of phosphoric acid, sulfuric acid, and nitric acid, and process for their preparation are disclosed in U.S. Pat. No. 4,365,061 said patent being incorporated herein by reference.

When used, the pH modifier is typically used at a level of from 0.01% to 10%, preferably from 0.1% to 5%, by weight of the composition.

Preparation of Solid Particulate Granular Fabric Softener

The granules can be formed by preparing a melt, solidifying it by cooling, and then grinding and sieving to the desired size. In a three-component mixture, e.g., nonionic surfactant, single-long-chain cationic, and DEQA, it is more preferred, when forming the granules, to pre-mix the nonionic surfactant and the more soluble single-long-chain alkyl cationic compound before mixing in a melt of the diester quaternary ammonium cationic compound.

It is highly preferred that the primary particles of the granules have a diameter of from 50 to 1,000, preferably from 50 to 400, more preferably from 50 to 200, microns. The granules can comprise smaller and larger particles, but preferably from 85% to 95%, more preferably from 95% to 100%, are within the indicated ranges. Smaller and larger particles do not provide optimum emulsions/dispersions when added to water. Other methods of preparing the primary particles can be used including spray cooling of the melt. The primary particles can be agglomerated to form a dust-free, non-tacky, free-flowing powder. The agglomeration can take place in a conventional agglomeration unit (i.e., Zig-Zag Blender, Lodige) by means of a water-soluble binder. Examples of water-soluble binders useful in the above agglomeration process include glycerol, polyethylene glycols, polymers such as PVA, polyacrylates, and natural polymers such as sugars.

The flowability of the granules can be improved by treating the surface of the granules with flow improvers such as clay, silica or zeolite particles, water-soluble inorganic salts, starch, etc.

Method of Use

Water can be added to the particulate, solid, granular compositions to form dilute or concentrated liquid softener compositions for later addition to the rinse cycle of the laundry process with a concentration of said biodegradable cationic softening compound of from 0.5% to 50%, preferably from 1% to 35%, more preferably from 4% to 32% by weight. The particulate, rinse-added solid composition (1) can also be used directly in the rinse bath to provide adequate usage concentration (e.g., from 10 to 1,000 ppm, preferably from 50 to 500 ppm, of total softener active ingredient). The liquid compositions can be added to the rinse to provide the same usage concentrations.

The water temperature for preparation should be from 20° C. to 90° C., preferably from 25° C. to 80° C. Single-long-chain alkyl cationic surfactants as the viscosity/dispersibility modifier at a level of from 0% to 15%, preferably from 3% to 15%, more preferably from 5% to 15%, by weight of the composition, are preferred for the solid composition. Nonionic surfactants at a level of from 5% to 20%, preferably from 8% to 15%, as well as mixtures of these agents can also serve effectively as the viscosity/dispersibility modifier.

The emulsified/dispersed particles, formed when the said granules are added to water to form aqueous concentrates, typically have an average particle size of less than 10 microns, preferably less than 2 microns, and more preferably from 0.2 to 2 microns, in order that effective deposition onto fabrics is achieved. The term "average particle size," in the context of this specification, means a number average particle size, i.e., more than 50% of the particles have a diameter less than the specified size.

Particle size for the emulsified/dispersed particles is determined using, e.g., a Malvern particle size analyzer.

Depending upon the particular selection of nonionic and cationic surfactant, it may be desirable in certain cases, when using the solids to prepare the liquid, to employ an efficient means for dispersing and emulsifying the particles (e.g., blender).

Solid particulate compositions used to make liquid compositions can, optionally, contain electrolytes, perfume, antifoam agents, flow aids (e.g., silica), dye, preservatives, and/or other optional ingredients described hereinbefore.

The benefits of adding water to the particulate solid composition to form aqueous compositions to be added later to the rinse bath include the ability to transport less weight thereby making shipping more economical, and the ability to form liquid compositions similar to those that are normally sold to consumers, e.g., those that are described herein, with lower energy input (i.e., less shear and/or lower temperature). Furthermore, the particulate granular solid fabric softener compositions, when sold directly to the consumers, have less packaging requirements and smaller, more disposable containers. The consumers will then add the compositions to available, more permanent, containers, and add water to pre-dilute the compositions, which are then ready for use in the rinse bath, just like the liquid compositions herein. The liquid form is easier to handle, since it simplifies measuring and dispensing.

2. Dryer Activated Compositions

The present invention also relates to improved solid dryer-activated fabric softener compositions which are either (A) incorporated into articles of manufacture, e.g., on a substrate, or, are (B) in the form of particles similar to those disclosed above. (including, where appropriate, agglomerates, pellets, and tablets of said particles). Such compositions typically contain from 10% to 95% of fabric softening agent.

A. Substrate Articles

In preferred embodiments, the present invention encompasses articles of manufacture. Representative articles are those that are adapted for use to provide unique perfume benefits and to soften fabrics in an automatic laundry dryer, of the types disclosed in U.S. Pat. Nos.: 3,989,631; 4,055, 248; 4,073,996; 4,022,938; 4,764,289; 4,808,086; 4,103, 047; 3,736,668; 3,701,202; 3,634,947; 3,633,538; and 3,435,537; and 4,000,340,, all of said patents being incorporated herein by reference.

Typical articles of manufacture of this type include articles comprising:

I. a fabric conditioning composition comprising from 30% to 95% of normally solid, dryer softenable fabric softening agent comprising said biodegradable fabric softening active; and II. a dispensing means which provides for release of an effective amount of said composition including an effective amount of ii, sufficient to provide odor control, to fabrics in an automatic laundry dryer at automatic laundry dryer operating temperatures, e.g., from 35° C. to 115° C.

When the dispensing means is a flexible substrate, e.g., in sheet configuration, the fabric conditioning composition is releasably affixed on the substrate to provide a weight ratio of conditioning composition to dry substrate ranging from 10:1 to 0.5:1, preferably from 5:1 to 1:1.

The solid fabric softener compositions herein can include cationic and nonionic fabric softener actives used in combination with each other.

D-EXAMPLES

The synthesis of the fabric softening compound of the present invention is further illustrated in the following Synthesis Examples. These Synthesis Examples are provided for purposes of illustration only.

Fatty Acid Compound Synthesis Example A 1,300 grams of food grade (refined, bleached, degummed) canola oil and approximately 6.5 grams of a commercial nickel hydrogenation catalyst (Engelhard, "N-545"®) corresponding to approximately 0.13 wt. % Ni, are placed in a hydrogenation reactor which is equipped with stirrer. The reactor is sealed and evacuated. The contents are heated to 170° C. and hydrogen is fed into the reactor. Stirring at 450 rpm is maintained throughout the reaction. After 10 minutes the temperature in the reactor is 191° C. and the hydrogen pressure is 11 psig. The temperature is held at 190° C. After 127 minutes from when the hydrogen feed began, the hydrogen pressure is 10 psig. A sample of the reaction mass is drawn and found to have an Iodine Value of 78.0 and a cis:trans ratio of 1.098. After another 20 minutes at 190° C., the hydrogen pressure is 9.8 psig. The hydrogen feed is discontinued and the reactor contents cooled with stirring. The final reaction product has an Iodine Value of 74.5 and a cis:trans ratio of 1.35.

The product that forms in the reactor is removed and filtered. It has a cloud point of 22.2° C. The chain length distributions of the acyl substituents on the sample taken at 127 minutes, and of the final product, are determined to be as shown in Table 1 in which "sat." means saturated, and "mono" and "di" means monounsaturated and diunsaturated, respectively.

TABLE 1

| Chain length | Approximate Percent (mol.) | |
| --- | --- | --- |
| | Sample @ 127 min. | Product |
| C14-sat. | 0.1 | 0.1 |
| C16-sat. | 4.7 | 4.6 |
| C16-mono. | 0.4 | 0.4 |
| C18-sat. | 8.9 | 13.25 |
| C18-mono. | 77.0 | 73.8 |
| C18-di. | 4.5 | 3.1 |
| C20-sat. | 0.7 | 0.75 |
| C-20-mono. | 2.1 | 2.0 |
| Other | 1.6 | 2.0 |

Fatty Acid Compound Synthesis Example B 1,300 grams of food grade canola oil and 5.2 grams of Engelhard "N-545" ® nickel hydrogenation catalyst are placed in a hydrogenation reactor which is equipped with a stirrer. The reactor is sealed and evacuated. The contents are heated to 175° C. and hydrogen is fed into the reactor. Stirring is maintained at 450 rpm throughout the course of reaction. After 5 minutes the temperature in the reactor is 190° C. and the hydrogen pressure is 7 psig.

The temperature is held at 190° C. After 125 minutes from the start of the hydrogen feed, the hydrogen pressure is 7 psig. A sample of the reaction mass is drawn and found to have an Iodine Value of 85.4. After another 20 minutes at 190° C., the hydrogen pressure is 6 psig. The hydrogen feed is discontinued and the reactor contents cooled with stirring. The final reaction product has an Iodine Value of 80.0. The product that forms in the reactor is removed and filtered. It has a cloud point of 18.6° C.

Fatty Acid Compound Synthesis Example C 1,300 grams of food grade canola oil and 2.9 grams of Engelhard "N-545" nickel hydrogenation catalyst are placed in a hydrogenation reactor which is equipped with a stirrer. The reactor is sealed and evacuated. The contents are heated to 180° C. and hydrogen is fed into the reactor. Stirring is maintained at 450 rpm throughout the course of the reaction. After 5minutes the temperature in the reactor is 192° C. and the hydrogen pressure is 10 psig. The temperature is held at 190±3° C. After 105 minutes from the start of the hydrogen feed, the hydrogen pressure is 10 psig. A sample of the reaction mass is drawn and found to have an Iodine Value of 85.5. After another 20 minutes at 190° C., the hydrogen pressure is 10 psig. The hydrogen feed is discontinued and the reactor contents cooled with stirring. The final reaction product has an Iodine Value of 82.4. The product that forms in the reactor is removed and filtered. It has a cloud point of 17.2° C.

Fatty Acid Compound Synthesis Example D 1,300 grams of food grade canola oil and 1.4 grams of Engelhard "N-545"® nickel hydrogenation catalyst are placed in a hydrogenation reactor which is equipped with a stirrer. The reactor is sealed and evacuated. The contents are heated to 180° C. and hydrogen is fed into the reactor. After 5 minutes the temperature in the reactor is 191° C. and the hydrogen pressure is 10 psig. The temperature is held at 190±3° C. After 100 minutes from the start of the hydrogen feed, the hydrogen pressure is 10 psig. A sample of the reaction mass is drawn and found to have an Iodine Value of 95.4. After another 20 minutes at 190° C., the hydrogen pressure is 10 psig. The hydrogen feed is discontinued and the reactor contents cooled with stirring. The final reaction product had an Iodine Value of 2.3. The product that forms in the reactor is removed and filtered. It has a cloud point of 34° C.

Fatty Acid Compound Synthesis Example E 1,300 grams of food grade canola oil and 1.3 grams of Engelhard "N-545" ® nickel hydrogenation catalyst are placed in a hydrogenation reactor which is equipped with a stirrer. The reactor is sealed and evacuated. The contents are heated to 190° C. and hydrogen is fed into the reactor to a hydrogen pressure of 5 psig. After 3 hours from the start of the hydrogen feed, a sample of the reaction mass is drawn and found to have an iodine value of 98. The hydrogenation is interrupted, another 0.7 grams of the same catalyst is added, and the reaction conditions are reestablished at 190° C. for another 1 hour. The hydrogen feed is then discontinued and the reactor contents cooled with stirring. The final reaction product had an Iodine Value of 89.9. The product that forms in the reactor is removed and filtered. It has a cloud point of 16.0° C.

Fatty Acid Compound Synthesis Example F 1,300 grams of food grade canola oil and 2.0 grams of Engelhard "N-545"® nickel hydrogenation catalyst are placed in a hydrogenation reactor which is equipped with a stirrer. The reactor is sealed and evacuated. The contents are heated to 190° C. and hydrogen is fed into the reactor to a hydrogen pressure of 5 psig. Stirring is maintained at 420 rpm throughout the course of reaction of the hydrogen feed. After 130 minutes from the start of the hydrogen feed, the hydrogen feed is discontinued and the reactor contents cooled with stirring. The final reaction product had an Iodine Value of 96.4. The product that forms in the reactor is removed and filtered. It has a cloud point of 11.2° C.

Fatty acid Compound Synthesis Example G

A mixture of 1,200 grams of the hydrogenated oil from Synthesis Example F and 200 grams of the hydrogenated oil from Synthesis Example A is hydrolyzed three times with 250° C. steam at 600 psig for 2.5 hours at a ratio of steam:oil of 1.2 (by weight). An aqueous solution containing the glycerine which had split off is removed.

The resulting mixture of fatty acids is vacuum distilled for a total of 150 minutes, in which the pot temperature rose gradually from 200° C. to 238° C. and the head temperature rose gradually from 175° C. to 197° C. Vacuum of 0.3–0.6 mm is maintained.

The fatty acids product of the vacuum distillation has an Iodine Value of 99.1, an amine value (AV) of 197.6 and a saponification value (SAP) of 198.6.

The following are synthesis examples of softener compounds aacording to the present invention:

Synthesis Example of Softener Compound 1

1)-Esterification:

489 grams of partly hydrogenated tallow fatty acid with an IV of 45 and an Acid Value of 206, commercially available under the tradename Distal 51 and sold by Witco Corporation, is added into the reactor, the reactor is flushed with N2 and 149 grams of triethanolamine is added under agitation. The molar ratio of fatty acid to triethanol amine is of 1.8:1. The mixture is heated above 150 C and the pressure is reduced to remove the water of condensation. The reaction is prolonged until an Acid Value of 5 is reached.

The above mentioned partly hydrogenated tallow fatty acid is also commercially available from Henkel under the tradename Edenor HtiCT, or commercially available from Unichema under the tradename Prifac 5905.

2)-Quaternization:

To 627 grams of the product of condensation, 122 grams of dimethylsulfate is added under continuous agitation. The reaction mixture is kept above 50° C. and the reaction is followed by verifying the residual amine value. 749 grams of softener compound of the invention is obtained.

The quaternized material is optionally diluted with e.g. 15% of isopropanol which lower the melting point of the material thereby providing a better ease in the handling of the material.

Synthesis Example of Softener Compound 2

1)-Esterification:

504 grams of oleic fatty acid with an IV of 90 and an Acid Value of 198, commercially available under the tradename Emersol 233 and sold by Henkel Corporation, is added into the reactor, the reactor is flushed with N2 and 149 grams of triethanolamine is added under agitation. The molar ratio of fatty acid to triethanol amine is of 1.8:1. The mixture is heated above 150 C and the pressure is reduced to remove the water of condensation. The reaction is prolonged until an Acid Value of 2 is reached.

The above mentioned oleic fatty acid is also commercially available from Henkel under the tradename Edenor TiO5.

2)-Quaternization:

To the 629 grams of the product of condensation 122 grams of dimethylsulfate is added under continuous agitation. The reaction mixture is kept above 50 C and the reaction is followed by verifying the residual amine value.

751 grams of softener compound of the invention is obtained.

The quaternized material is optionally diluted with e.g. 8% of ethanol which lower the melting point of the material thereby providing a better ease in the handling of the material.

Synthesis Example of softener compound 3
1-Esterification:

571 grams of Canola fatty acid with an IV of about 100 and an Acid Value of about 196 as made according to Fatty Acid Compound Synthesis Example G is added into the reactor, the reactor is flushed with N2 and 149 grams of triethanolamine is added under agitation. The molar ratio of fatty acid to triethanol amine is of 2.0:1. The mixture is heated above 150 C and the pressure is reduced to remove the water of condensation. The reaction is prolonged until an Acid Value of 3 is reached.

2)-Quaternization:

To the 698 grammes of the product of condensation 122 grams of dimethylsulfate is added under continuous agitation. The reaction mixture is kept above 50 C and the reaction is followed by verifying the residual amine value.

820 grams of softener compound of the invention is obtained.

The quaternized material is optionally diluted with e.g. 15% of a 50:50 ethanol/hexyleneglycol mixture which lower the melting point of the material thereby providing a better ease in the handling of the material.

Synthesis Example of Softener Compound 4
1)-Esterification:

457 grams of Canola fatty acid with an IV of about 100 and an Acid Value of about 196, as made according to Fatty Acid Compound Synthesis Example G, is added into the reactor, the reactor is flushed with N2 and 149 grams of triethanolamine is added under agitation. The molar ratio of fatty acid to triethanol amine is of 1.6:1. The mixture is heated above 150 C and the pressure is reduced to remove the water of condensation. The reaction is prolonged until an Acid Value of 1 is reached.

2)-Quaternization:

To the 582 grams of the product of condensation 122 grams of dimethylsulfate is added under continuous agitation. The reaction mixture is kept above 50 C and the reaction is followed by verifying the residual amine value.

704 grams of softener compound of the invention is obtained.

The quaternized material is optionally diluted with e.g. 8% of ethanol which lower the melting point of the material thereby providing a better ease in the handling of the material.

The above synthesised softener compound are also exemplified below in the non-limiting fabric softening composition examples.

Abbreviations used in the Examples

In the softening compositions, the abreviated component identification have the following meanings:

Softener compound 1: Softener compound as made according to Synthesis Example of softener compound 1

Softener compound 2: Softener compound as made according to Synthesis Example of softener compound 2

Softener compound 3: Softener compound as made according to Synthesis Example of softener compound 3

Softener compound 4: Softener compound as made according to Synthesis Example of softener compound 4

IPA: Isopropylalcohol
TMPD: 2,2,4-trimethyl-1,3-pentanediol
CHDM: 1,4 cyclohexanedimethanol

|  | 1 | 2 | 3 | 4 | 5 |
|---|---|---|---|---|---|
| Softener compound 1 | 8.0 | — | — | — | — |
| Softener compound 2 | — | 8.0 | 20 | 30 | 28 |
| IPA | 1.4 | — | — | — | — |
| Ethanol | — | 0.7 | 1.7 | 2.6 | 2.4 |
| 1,2 Hexanediol | — | 10 | 15 | — | — |
| 2-ethyl-1,3-hexanediol | — | — | — | — | 12 |
| TMPD | — | — | — | 12 | — |
| CHDM | — | — | — | 5 | 5 |
| HCl | 0.02 | 0.02 | 0.02 | 0.02 | 0.02 |
| Calcium chloride | 0.04 | — | — | — | — |
| Perfume | 0.5 | 0.5 | 1.0 | 2.0 | 2.0 |
| Dye | 5 ppm | 5 ppm | 5 ppm | 5 ppm | 5 ppm |
| Deminerised water | Balance | Balance | Balance | Balance | Balance |

|  | 6 | 7 | 8 | 9 |
|---|---|---|---|---|
| Softener compound 3 | 8.0 | 25 | — | 28 |
| Softener compound 4 | — | — | 30 | — |
| Ethanol | 0.7 | 2.2 | 2.6 | 2.5 |
| Hexylene glycol | 0.7 | 2.2 | — | 2.5 |
| 1,2 Hexanediol | 9 | 12 | 15 | 5 |
| TMPD | — | 5 | — | 9 |
| HCl | 0.02 | 0.02 | 0.02 | 0.02 |
| Perfume | 0.5 | 1.5 | 1.0 | 2.0 |
| Dye | 5 ppm | 20 ppm | 20 ppm | 5 ppm |
| Demin water | Balance | Balance | Balance | Balance |

What is claimed is:

1. A clear liquid fabric softening composition comprising
   a) a biodegradable fabric softener compound, wherein the softener compound comprises a quaternary ammonium salt, the quaternised ammonium salt being a quaternised product of a condensation product between:
      i) a fraction of saturated or unsaturated, linear or branched fatty acids, or of derivatives of said acids, said fatty acids or derivatives each possessing a hydrocarbon chain in which the number of atoms is between 5 and 21, and
      ii) triethanolamine,
   characterized in that said condensation product has an acid value measured by titration of the condensation product with a standard solution against a phenolphthalein indicator, of less than 6.5 and wherein the mole ratio of i) to ii) is from 1.8:1 to 2.2:1;
   b) water; and
   c) principal solvent in an amount effective to provide a clear composition.

2. A clear liquid fabric softening composition according to claim 1, wherein the fatty acid/triethanolamine mole ratio is 2.0:1.

3. A clear liquid fabric softening composition according to claim 1, wherein the biodegradable fabric softener compound has an acid value of less than 5.

4. A clear liquid fabric softening composition according to claim 1, wherein the biodegradable fabric softener compound has an acid value of less than 3.

5. A clear liquid fabric softening composition according to claim 1, wherein the biodegradable fabric softener compound has the formula:

wherein each R substituent is hydrogen or a short chain $C_1$–$C_6$ alkyl or hydroxyalkyl group;

each m is 2 or 3; n is 2; each Y is —O—(O)C—, —(R)N—(O)C—, —C(O)—N(R)—, or —C(O)—O—; the sum of carbons in each $R^1$, plus one when Y is —O—(O)C— or —(R)N—(O)C—, is $C_6$–$C_{22}$, but no more than one $R^1$, or $YR^1$, sum being less than 12 and then the other $R^1$, or $YR^1$, sum is at least 16, with each $R^1$ comprising a long chain $C_5$–$C_{21}$ branched alkyl or unsaturated alkyl, optionally substituted, the ratio of branched alkyl to unsaturated alkyl being from 5:95 to 95:5, and for the unsaturated alkyl group, the Iodine Value of the parent fatty acid of this $R^1$ group is from 20 to 140, and wherein the counterion, $X^-$ is a softener-compatible anion.

6. A biodegradable fabric softener compound according to claim 1, wherein the fatty acid fraction contains cis and trans isomers with a cis/trans ratio of from 1:1 to 50:1.

7. A clear liquid fabric softening composition according to claim 1, wherein the principal solvent is selected from mon-ols, C6 diols, C7 diols, octanediol isomers, butanediol derivatives, trimethylpentanediol isomers, ethylmethylpentanediol isomers, propyl pentanediol isomers, dimethylhexanediol isomers, ethylhexanediol isomers, methylheptanediol isomers, octanediol isomers, nonanediol isomers, alkyl glyceryl ethers, di(hydroxy alkyl) ethers, and aryl glyceryl ethers, aromatic glyceryl ethers, alicyclic diols and derivatives, $C_3C_7$ diol alkloxylated derivatives, aromatic diols, and unsaturated diols, and mixtures thereof.

8. A clear liquid fabric softening composition according to claim 1, wherein the mole ratio of i) to ii) is from 2.0:1 to 2.2:1.

9. A clear liquid fabric softening composition comprising
a) a biodegradable fabric softener compound, the softener compound comprising a quaternary ammonium salt, the quaternised ammonium salt being a quaternised product of a condensation product between:
i) a fraction of saturated or unsaturated, linear or branched fatty acids, or of derivatives of said acids, said fatty acids or derivatives each possessing a hydrocarbon chain in which the number of atoms is between 5 and 21, and
ii) triethanolamine,
characterized in that said condensation product has an acid value measured by titration of the condensation product with a standard solution against a phenolphthalein indicator, of less than 6.5, said biodegradable fabric softener compound is present in an amount of from 1% to 80%, by weight of the composition; and
b) a principal solvent having a ClogP of from 0.15 to 0.64 in an amount from 6% to less than 40% by weight of the composition and effective to provide a clear composition.

10. A fabric softening composition according to claim 9, wherein said principal solvent is selected from monols, C6 diols, C7 diols, butanediol derivatives, trimethylpentanediol isomers, ethylmethylpentanediol isomers, propyl pentanediol isomers, dimethylhexanediol isomers, ethylhexanediol isomers, methylheptanediol isomers, octanediol isomers, nonanediol isomers, alkyl glyceryl ethers, di(hydroxy alkyl) ethers, and aryl glyceryl ethers, aromatic glyceryl ethers, alicyclic diols and derivatives, $C_3$–$C_7$ diol alkloxylated derivatives, aromatic diols, and unsaturated diols, and mixtures thereof.

11. A fabric softening composition according to claim 10, wherein the principal solvent is selected from 2,2,4-trimethyl-1,3-pentanediol, ethoxylates of 2,2,4-trimethyl-1,3-pentanediol, 1,2 hexanediol, ethoxylates of 2-ethyl-1,3-hexanediol, 1,2 cyclohexanedimethanol, and mixtures thereof.

12. A fabric softening composition according to claim 11, wherein said principal solvent is present in a combination form of 2,2,4-trimethyl-1,3-pentanediol and 1,2 hexanediol.

13. A fabric softening composition according to claim 9, wherein said composition comprises an effective amount, sufficient to improve clarity, of low molecular weight water soluble solvents selected from the group consisting of: ethanol, isopropanol, propylene glycol, 1,3-propanediol, propylene carbonate, 1,4 cyclohexanedimethanol and mixtures thereof, said water soluble solvents being at a level that will not form clear compositions by themselves.

14. A premix composition comprising
a) a fabric softener compound comprising a quaternary ammonium salt, the quaternised ammonium salt being a quaternised product of a condensation product between:
i) a fraction of saturated or unsaturated, linear or branched fatty acids, or of derivatives of said acids, said fatty acids or derivatives each possessing a hydrocarbon chain in which the number of atoms is between 5 and 21, and
ii) triethanolamine,
characterized in that said condensation product has an acid value measured by titration of the condensation product with a standard solution against a phenolphthalein indicator, of less than 6.5; and b) at least one component selected from the group consisting of principal solvents, low molecular weight water soluble solvents, water soluble calcium salt, water soluble magnesium salt, perfume and mixtures thereof,
the premix having a viscosity of less than 1,000 cps.

15. A clear fabric softening composition comprising
a) a biodegradable fabric softening compound comprising a quaternary ammonium salt, the quaternary ammonium salt being a quaternised product of a condensation product between:
i) a fraction of saturated or unsaturated, linear or branched fatty acids, or of derivatives of said acids, said fatty acids or derivatives each possessing a hydrocarbon chain in which the number of atoms is between 5 and 21, and
ii) alkanolamine having alkanol groups of 1 to 4 carbon atoms,
characterized in that said condensation product has an acid value measured by titration of the condensation product with a standard solution against a phenolphthalein indicator, of less than 6.5 and wherein the mole ratio of i) to ii) is from 1.8:1 to 2.2:1, the compound having the formula:

wherein each R substituent is hydrogen or a short chain $C_1$–$C_6$ alkyl or hydroxyalkyl group; each m is 2 or 3; each n is from 1 to 4; each Y is —O—(O)C—, —(R)N—(O)C—, —C(O)—N(R)—, or —C(O)—O—; the sum of carbons in each $R^1$, plus one when Y is —O—(O)C— or —(R)N—(O)C—, is $C_6$–$C_{22}$, but not more than one $R^1$, or $YR^1$, sum being less than 12 and then the other $R^1$, or $YR^1$, sum is at least 16, with each $R^1$ comprising a long chain $C_5$–$C_{21}$ branched alkyl or unsaturated alkyl, optionally substituted, the ratio of branched alkyl to unsaturated alkyl being from 5:95 to 95:5, and for the unsaturated alkyl group, the Iodine Value of the parent fatty acid of this $R^1$ group is from 20 to 140, and wherein the counterion, X— is a softener-compatible anion;

b) water; and c) principal solvent, in an amount effective to provide a clear composition.

* * * * *